(12) United States Patent
Zhao

(10) Patent No.: US 9,945,792 B2
(45) Date of Patent: Apr. 17, 2018

(54) GENERATING AN ARRAY OF SPOTS ON INCLINED SURFACES

(71) Applicant: KLA-Tencor Corporation, Milpitas, CA (US)

(72) Inventor: Guoheng Zhao, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 721 days.

(21) Appl. No.: 13/719,928

(22) Filed: Dec. 19, 2012

(65) Prior Publication Data

US 2014/0168774 A1   Jun. 19, 2014

(51) Int. Cl.
*G02B 5/18* (2006.01)
*G02B 27/44* (2006.01)
*G01N 21/95* (2006.01)
*G02B 27/09* (2006.01)
*G01N 21/88* (2006.01)
(Continued)

(52) U.S. Cl.
CPC ..... *G01N 21/9501* (2013.01); *G01N 21/8806* (2013.01); *G01N 21/956* (2013.01); *G02B 27/0905* (2013.01); *G02B 27/0944* (2013.01); *G02B 27/425* (2013.01)

(58) Field of Classification Search
CPC ............. G01N 21/9501; G01N 21/956; G01N 21/8806; G01N 21/95623; G02B 27/0905; G02B 27/0944; G02B 27/0037; G02B 27/0056; G02B 27/42; G02B 27/4205; G02B 27/4233; G02B 5/008; G02B 5/18; G02B 5/32; G02B 5/203; G02B 5/0252; G02B 5/1876; G02B 6/2931; G02B 6/29308; G02B 6/29313; G02B 6/29314; G02B 6/29316; G02B 6/29322; G02B 6/29326; G02B 6/29328; G02B 6/02195; G02B 6/3516; G02B 6/3534; G03F 7/702; G03F 7/70108
USPC ................... 359/558, 566; 348/126, E7.085; 356/237.2
See application file for complete search history.

(56) References Cited

U.S. PATENT DOCUMENTS 5,633,735 A * 5/1997 Hunter, Jr. ........... B23K 26/067
                                                        219/121.68
5,889,593 A    3/1999 Bareket
5,978,139 A   11/1999 Hatakoshi et al.
(Continued)

FOREIGN PATENT DOCUMENTS

EP     1804091 B1    7/2007
EP     2378319 A1   10/2011

*Primary Examiner* — Mustak Choudhury
(74) *Attorney, Agent, or Firm* — Suiter Swantz pc llo

(57) ABSTRACT

A system which may be used to generate a plurality of spots on a surface is provided. The spots may be aligned with the incident plane of oblique illumination. The system may include a diffractive optical element configured to split a beam into a plurality of beams by generating a plurality of diffraction orders. The system may also include a focusing lens configured to focus at least some of the plurality of beams on the surface in the plurality of spots. At least some of the plurality of beams may be focused on the surface at an oblique illumination angle. The system may also include an illumination source positioned off-axis relative to an optical axis of the diffractive optical element. Using the system, a plurality of spots may be generated on an inclined surface.

20 Claims, 9 Drawing Sheets

(51) Int. Cl.
*G01N 21/956* (2006.01)
*G02B 27/42* (2006.01)

(56) References Cited

U.S. PATENT DOCUMENTS

| | | | |
|---|---|---|---|
| 7,345,752 | B1 | 3/2008 | Kadkly et al. |
| 7,489,393 | B2 | 2/2009 | Biellak et al. |
| 8,194,301 | B2 | 6/2012 | Zhao et al. |
| 2001/0048521 | A1* | 12/2001 | Vaez-Iravani ........ G01N 21/956 356/237.2 |
| 2004/0042001 | A1* | 3/2004 | Vaez-Iravani ...... G01N 21/8806 356/237.2 |
| 2004/0225399 | A1 | 11/2004 | Chen et al. |
| 2006/0055905 | A1* | 3/2006 | Baselmans .......... G03F 7/70058 355/67 |
| 2007/0229833 | A1* | 10/2007 | Rosencwaig et al. ........ 356/426 |
| 2009/0040525 | A1* | 2/2009 | Kadkly .............. G01N 21/9501 356/446 |

* cited by examiner

GENERATING AN ARRAY OF SPOTS ON INCLINED SURFACES

TECHNICAL FIELD

The disclosure generally relates to the field of wafer inspection, and more particularly to a system and method for generating an array of spots on an inclined surface.

BACKGROUND

Current systems and methods for generating an array of spots on an inclined surface may not provide a required level of performance. For example, in some systems the spot arrangement may be tangential, meaning that the spots are largely aligned with the tangential direction of a spiral scanning stage movement along with a small tilt. A drawback of tangential spot placement is that the pitch (the difference of scanning radius between adjacent spots) may not be exactly identical for all of the spots even when the spots are essentially equally spaced. This uneven spacing may be referred to as the "pitch error". The pitch error may be minimal for a surface having a large radius, such as the edge of a large wafer, but the pitch error may increase near the center of the wafer. The pitch error may change as the spots scan the wafer from the edge of the wafer to the center of the wafer, which can make the pitch error difficult to correct. Although ways to compensate for the pitch error do exist, these options may result in some loss of sensitivity or throughput for the system.

Therefore, there exists a need for improved systems and methods for generating an array of spots on an inclined surface.

SUMMARY

The present disclosure is directed to a system which may be used to generate a plurality of spots on a surface. The spots may be aligned with the incident plane of oblique illumination. The system may also include a diffractive optical element. The diffractive optical element may be configured to split a beam into a plurality of beams by generating a plurality of diffraction orders. The system may also include a focusing lens positioned adjacent to the diffractive optical element. The focusing lens may be configured to focus at least some of the plurality of beams on the surface in the plurality of spots. At least some of the plurality of beams may be focused on the surface at an oblique illumination angle. The system may also include an illumination source, the illumination source configured to provide the beam to the diffractive optical element. The illumination source may be positioned off-axis relative to an optical axis of the diffractive optical element. The combination of the diffractive optical element and the focusing lens generates multiple focuses along the optical axis, as the focusing lens is configured to focus at least some of the plurality of beams on the surface in the plurality of spots. Using the lens and the diffractive optical element, the plurality of beams may be focused on the surface at an oblique illumination angle. In one embodiment, the system may be used to provide a plurality of spots on an inclined surface.

The present disclosure is also directed to a method for generating a plurality of spots on a surface. The method may include the step of inputting a beam to a diffractive optical element in an off-axis position relative to an optical axis of the diffractive optical element. The method may also include the step of splitting the beam into a plurality of beams via the diffractive optical element. A further step of the method is to focus at least some of the plurality of beams on the surface to create the plurality of spots, the at least some of the plurality of beams focused on the surface at an oblique illumination angle.

The present disclosure is also directed to a system for generating a plurality of spots on a surface of a wafer. The system includes a diffractive optical element. The diffractive optical element may be configured to split a beam into a plurality of beams by generating a plurality of diffraction orders. The system also includes a focusing lens positioned adjacent to the diffractive optical element. The focusing lens may be configured to focus at least some of the plurality of beams on the surface in the plurality of spots. The at least some of the plurality of beams may be focused on the surface at an oblique illumination angle. The system also includes an illumination source configured for providing the beam to the diffractive optical element. The illumination source may be positioned off-axis relative to an optical axis of the diffractive optical element. Using the system, the plurality of spots are positioned on the wafer in a radial direction, which may be the linear stage motion direction of the spiral scanning stage. In addition, an incident plane of the at least some of the plurality of beams is parallel to the radial direction.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Figure 1A:
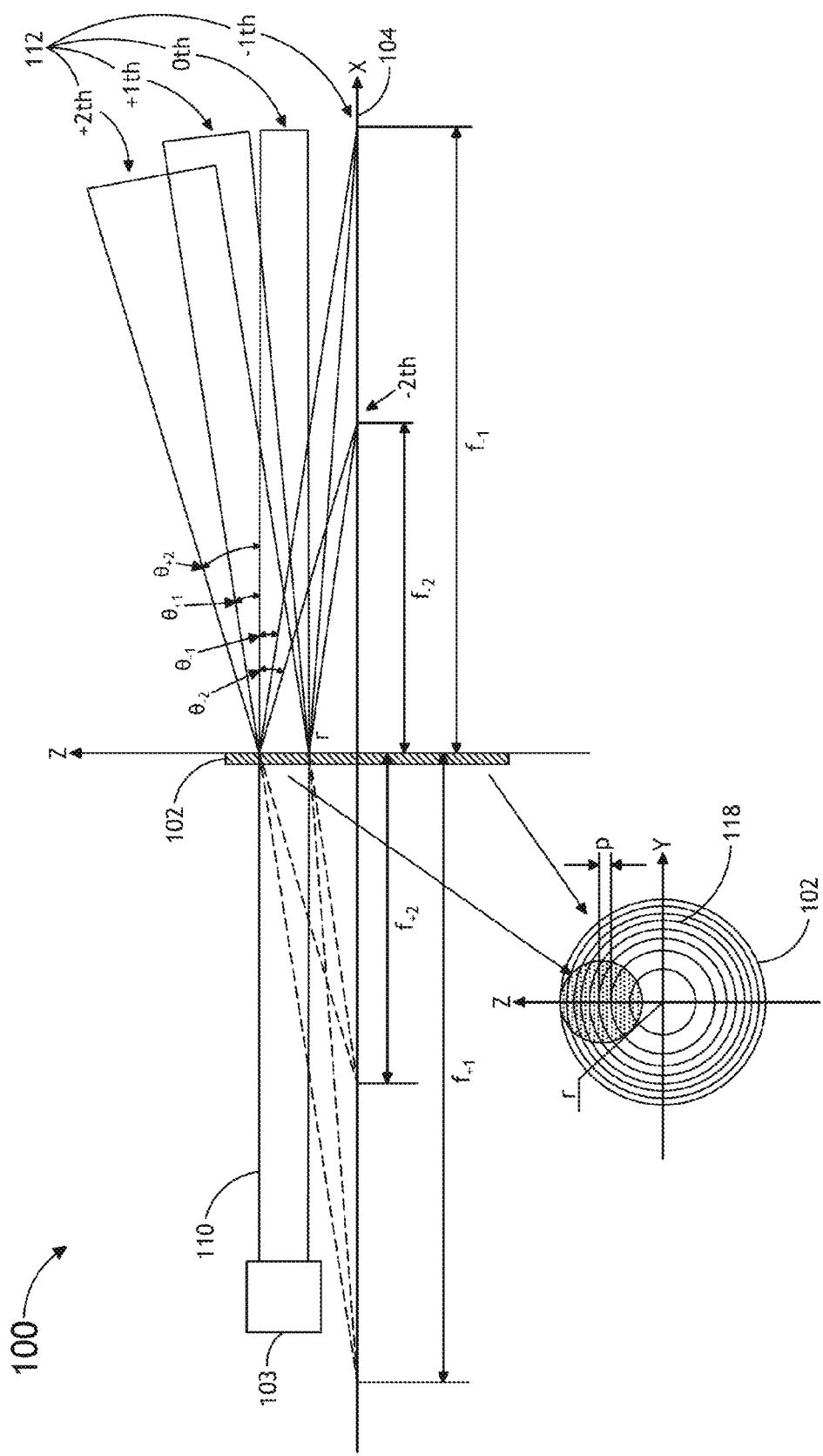
FIG. 1A shows a schematic diagram of a system for generating a plurality of spots on a surface.

Existing methods for generating an array of spots on a surface may include the use of a diffractive optical element (DOE) to first split a laser beam into multiple beams and then use a lens to focus the beams into an array of spots. The DOE may include a one dimensional grating, and the grating profile may be optimized for beam uniformity and diffraction efficiency.

The focal plane of the spot array may be perpendicular to the optical axis, which may be at an oblique incidence angle (for example, 70 degrees) with respect to the wafer surface. When using oblique illumination, in order to keep all of the spots in focus on the wafer surface, the line of the one dimensional spot array may be parallel to the wafer surface. As a result, the available array placement configurations may be limited. Similarly, the array placement may also require an offset in the radial direction between spots so that each spot scans a different track. The array placement may also require each spot in the array of spots to be elongated in the radial direction in order to maximize throughput within the limits of the spindle speed.

In order to offset the spots in the radial direction and elongate the spots in the radial direction, the incident plane may be tilted to an offset angle with respect to the radial direction. It may be possible to eliminate this tilt by generating the spot array while maintaining the incident plane to be parallel to the radial direction, but this technique can pose drawbacks.

Aspheric surfaces and tilt or decentered optical elements may be used to compensate for the focus offset when using oblique illumination. However, this may be effective only for a small range and for relatively large spot sizes.

In addition, existing systems for generating an array of spots on a surface may entail an arrangement that is often referred as "tangential spots". In a tangential spot array, the 1D array may be largely aligned with the tangential direction of spiral scanning with a small tilt. A drawback of tangential spots is that the pitch (that is, the difference of scanning radius between adjacent spots) may not be exactly identical for all spots, even though the spots are equally spaced. This difference in pitch between spots may be referred to as "pitch error". The pitch error may be minimal for a larger radius, such as at the edge of a 300 mm wafer, but the pitch error may increase towards the center of the wafer. Although it may be possible to compensate for the pitch error to some extent, existing methods may result in some loss of sensitivity or throughput.

In some cases, the spot array is aligned with the radial direction and at the same time the spot elongation should also be along the radial direction. This configuration requires the illumination optics be able to generate an array of spots on an inclined surface, and presents several challenges.

Therefore, there exists a need for an effective solution for generating a radial spot array that can generate a small spot size and a large number of spots in a large field at an oblique illumination angle. Similarly, there exists a need for such a system to be compatible with a large laser wavelength bandwidth.

Reference will now be made in detail to the subject matter disclosed, which is illustrated in the accompanying drawings. The present disclosure is directed to a system 100 as shown in FIG. 1A. The system 100 may be used to generate a plurality of spots on a surface. The system 100 may include a diffractive optical element 102 and an illumination source 103. The illumination source 103 may include a plurality of illumination sources in some embodiments. The illumination source 103 may be configured to provide illumination off-axis relative to an axis 104 of the diffractive optical element 102. The diffractive optical element 102 may be configured for generating a plurality of diffraction orders to split a beam 110 provided by the illumination source 103 into a plurality of beams 112.

The diffractive optical element 102 of the system 100 shown in FIG. 1A may include a diffractive optical element having concentric circles 118 of grating grooves as shown in FIG. 1A. The concentric circles 118 may cause the diffracted beams to converge to the optical axis 104 for positive diffraction orders. Similarly, the concentric circles 118 cause the diffracted beams to diverge from the optical axis 104 for negative diffraction orders. The groove pitch of the grating grooves 118 may be configured as a function of the radius of the diffractive optical element 102, so that each of the diffracted beams 112 has a real (for negative orders) or a virtual (for positive orders) focal point on the optical axis 104, and the focal points of different diffraction orders are at different positions on the optical axis 104. In one embodiment, the zeroth order of diffraction may remain a collimated beam if input beam 110 is a collimated beam. In order to have the nth diffraction order to be focused to a point on the optical axis 104, the grating pitch p as a function of radius r of diffractive optical element 102 follows the grating diffraction equation:

$$p = \frac{n\lambda}{\sin\theta_n} \qquad \text{eq. 1}$$

$$= \frac{-n\lambda}{\sin\left[\tan^{-1}\left(\frac{r}{f_n}\right)\right]}$$

Where $\lambda$ is the wavelength of light, n is the order of diffraction, $\theta_n$ is the angle between the light ray existing at diffractive optical element 102 at radius r and the optical axis 104, and $f_n$ is the focal length of the nth diffraction order.

According to equation 1, the grating pitch of the grating grooves 118 may be configured as a function of the radius of the diffractive optical element 102 for a specific diffraction order n such that substantially all of the light rays passing through the diffractive optical element 102 at different radii meet at the same (real or virtual) point on the optical axis 104 to achieve the desired focus. However, in some cases it may be difficult to configure the grating pitch p as a function of r for all the diffraction orders to simultaneously achieve a desired or perfect focus since the grating pitch (p) as a function of radius (r) changes with the order n of diffraction. As a result, it may be possible for only one diffraction order in addition to the zeroth order to be perfectly focused while other diffraction orders may have imperfect focus due to aberration of mis-matched grating pitches of the diffractive optical element 102.

The condition of simultaneous perfect focus for all diffraction orders can be met when the focal length $f_n$ is much larger than the radius of the diffractive optical element so that:

$$p \approx \frac{-n\lambda}{r} f_n = \frac{\lambda}{r} f_{-1} \qquad \text{eq. 2}$$

The grating pitch p as a function of radius r is independent of the diffraction order n, and the focal length of the nth diffraction order is given by the following equation:

$$f_n \approx \frac{-1}{n} f_{-1} \qquad \text{eq. 3}$$

Using only the diffractive optical element 102 may pose some problems for generating multiple spots of illumination. First, only the negative orders have a real focus while the other diffraction orders may have virtual focuses. Second, the focal lengths of different diffraction orders may not be equally spaced, and the spacing between focuses cannot be configured independent of the focal length. Third, the illumination angles of the diffraction orders may not be equal. Last, the constraints of very long focal lengths may make it difficult to generate small spots.

Figure 1B:
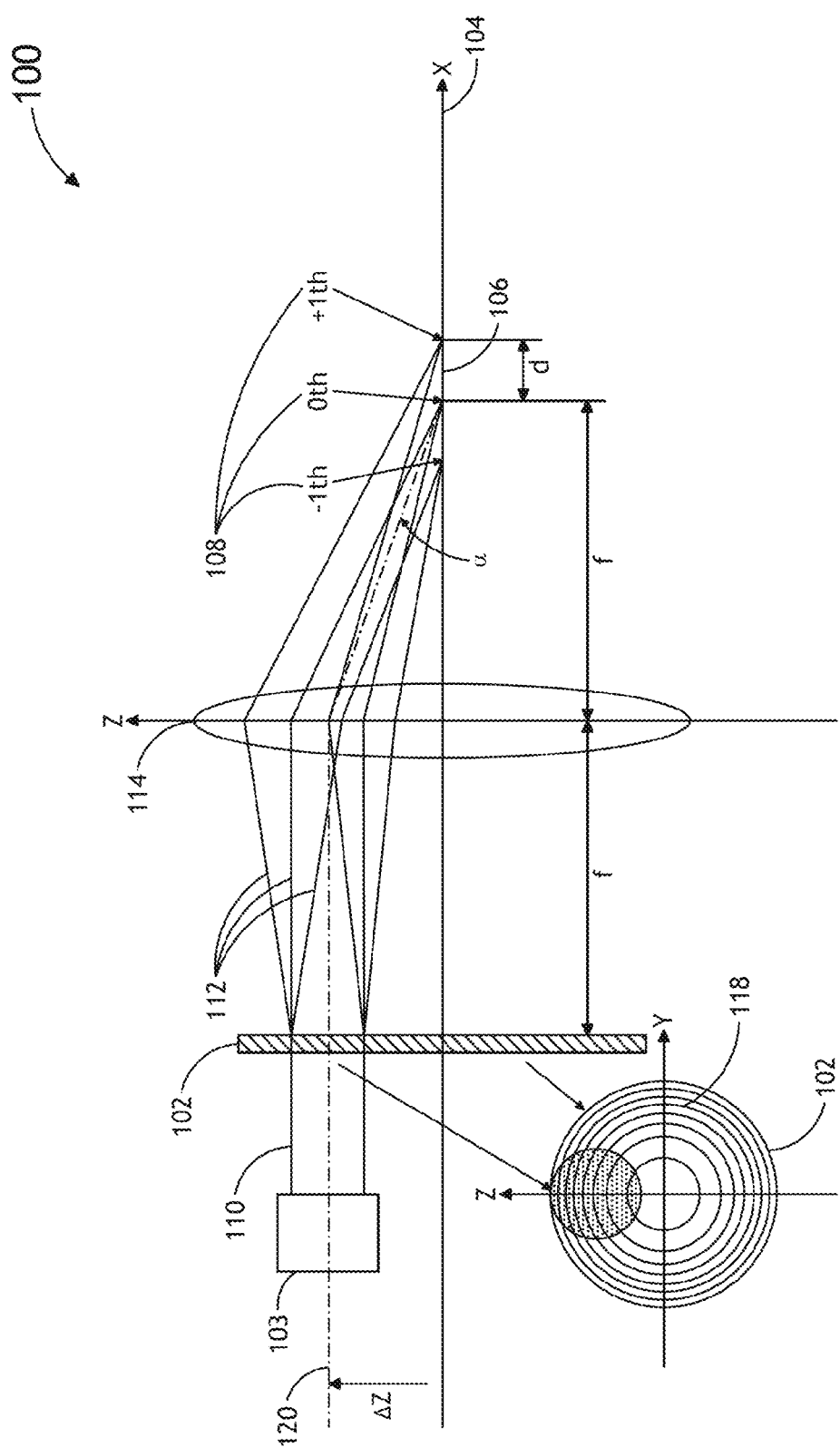
FIG. 1B shows a schematic diagram of a system for generating a plurality of spots on a surface.

The issues with generating multiple spots of illumination described in the previous paragraph may be addressed by including a focusing lens 114 having a focal length of f to the system 100. The embodiment of the system 100 including the focusing lens 114 is shown in FIG. 1B. The diffractive optical element 102 and lens 114 may be aligned to coincide at the optical axis 104. The diffractive optical element 102 may be placed at a distance of focal length f of lens 114 from lens 114, so that the incident angle (the angle between the chief ray/light beam of a diffraction order exiting lens 114 and the optical axis 104) are substantially the same or identical between all the diffraction orders. This coordination may be known as the telocentric condition, which improves uniform sensitivity between different spots for multi spot wafer inspection systems. The spacing d between the focal points of diffraction orders focused by lens 114 can be derived from the following paraxial lens equation:

$$\frac{1}{f_n} + \frac{1}{f + nd} = \frac{1}{f} \qquad \text{eq. 4}$$

If the spacing between spots is much smaller than the focal length f, that is, $$\frac{nd}{f} \ll 1,$$

equation 4 can be further simplified as follows:

$$d = \frac{f^2}{f_{-1}} \qquad \text{eq. 5}$$

The order number, n in equation 4 has been cancelled out in equation 5, therefore the spacing between the spots is uniform. The spacing between spots can be configured independent of the focal length f of lens 114 by selecting the proper value of $f_{-1}$, which in turn determines the grating pitch through equation 2.

The illumination angle α shown in FIG. 1B is determined by the offset ΔZ of the center of the input beam 110 provided by the illumination source 103 with the optical axis 104 of the diffractive optical element 102 and the focal length f of lens 114:

$$\tan\alpha = \frac{\Delta Z}{f} \qquad \text{eq. 6}$$

Equation 6 may change for different embodiments of the system 100. For example, equation 6 may change depending on the design of lens 114.

Using the lens 114 and the diffractive optical element 102, the plurality of beams 112 may be focused on the surface 106 at an oblique illumination angle. In one embodiment, the system 100 may be used to provide a plurality of spots on an inclined surface.

The system 100 shown in FIGS. 1A-1B also includes illumination source 103. The illumination source 103 is configured to provide the beam 110 to the diffractive optical element 102. The illumination source 103 may be positioned off-axis relative to the optical axis 104 of the diffractive optical element 102. The beam 110 may include a laser beam, or other beam type. The illumination source 103 may be a pulsed laser in one embodiment. In one example, the pulsed laser may have a spectral bandwidth of 35 pm to 100 pm. In another embodiment, the illumination source 103 may be a continuous wave laser. The type of laser used to provide the beam may depend on the system 100 design. For example, in some system 100 designs it may be necessary to correct for chromatic aberration in order to use the system 100 with a pulsed laser. This correction may not be required in implementations of the system 100 using continuous wave lasers.

The diffractive optical element 102 may include an axial diffractive optical element 102 that is aligned to coincide with the surface 106. In one embodiment, the diffractive optical element 102 may be a diffractive lens that can generate multiple diffraction orders. Similarly, the diffractive optical element 102 of the system 100 may include a single diffractive optical element 102 or a plurality of diffractive optical elements.

The grating profile of the diffractive optical element 102 may be designed such that the diffraction orders have substantially equal intensity. The grating profile may also be designed to provide improved diffraction efficiency of the diffraction orders. In one embodiment, the grating pitch of the diffractive optical element 102 may be in the range of 200 um to 800 um. In one example, the diffractive optical element 102 provides 11 diffraction orders ranging from −5 to +5.

The focusing lens 114 of the system 100 may include a single focusing lens 114 or a plurality of focusing lenses. In one example, the system 100 may include one diffractive optical element 102 and two focusing lenses 114. In one example, the focusing lens 114 is a refractive lens comprised of UV glass of fused silica.

Figure 2:
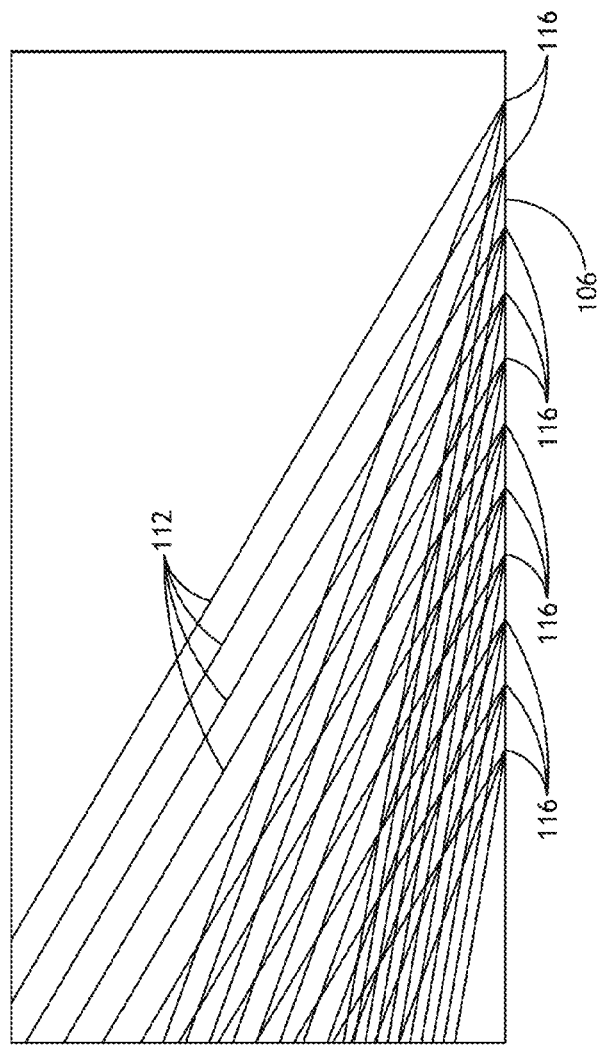
FIG. 2 shows an example of the placement of the spots on the surface using the system shown in FIG. 1.

An example of the placement of the spots 116 on the surface 106 using the system 100 shown in FIGS. 1A-1B is provided in FIG. 2. The plurality of beams 112/diffraction orders have been focused by the focusing lens 114 on to the surface 106 in a plurality of spots 116. In the embodiment shown in FIG. 2, the system 100 has provided eleven spots 116 on the surface 106. The spots 116 are spaced evenly apart in this embodiment in a one dimensional array in a single line along the surface 106. The incident angle of all the spots may be identical, shown in FIG. 2 by the parallel rays of the diffracted beams 112.

Figure 3:
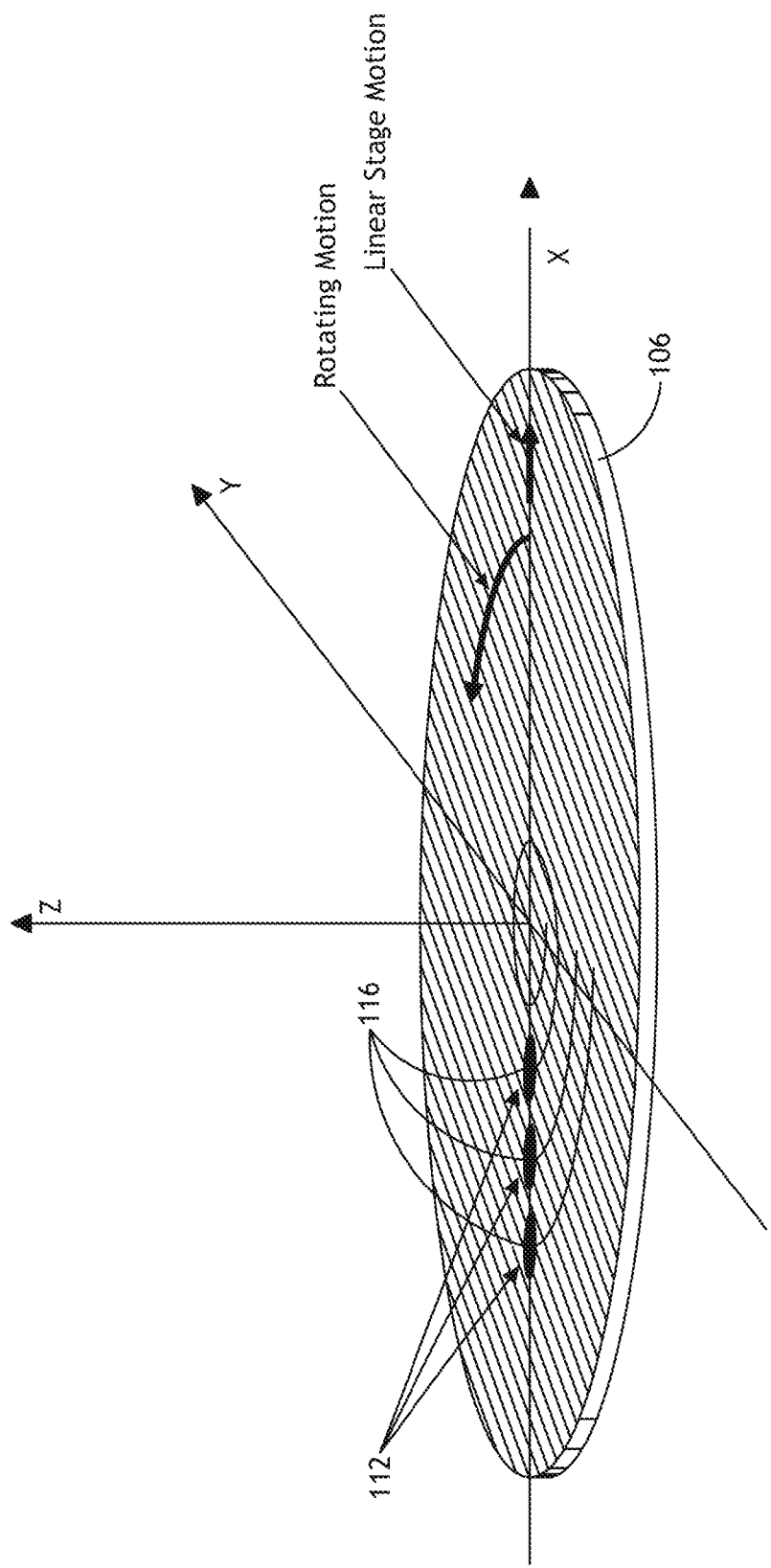
FIG. 3 illustrates the spot placement and stage motion direction of an embodiment of a system for generating a plurality of spots on a surface.

An embodiment of the system 100 implemented with a spiral scanning stage is shown in FIG. 3. As shown in FIG. 3, the plurality of spots 116 may be positioned in a radial direction parallel to a linear stage motion direction of the system 100. An example of the spot 116 placement and stage motion direction is shown in FIG. 3. The linear stage motion direction in FIG. 3 is in the direction of the X axis. The spots 116 are aligned in a radial direction that coincides with the stage motion direction. In addition, the spots 116 may also be elongated along the radial direction in one embodiment. This is due to the oblique incident angle of the plurality of beams 112. In one embodiment, it is advantageous to have elongated spot shape with its longer dimension aligned in the direction of the x-axis because this may provide faster inspection speed. Similarly, an incident plane of the plurality of beams 112 may also be parallel to the radial direction. In other words, the chief ray of the incident beams 112 is parallel to the plane of the x-axis and the z axis, where the z-axis is perpendicular to the surface 106.

Figure 4:
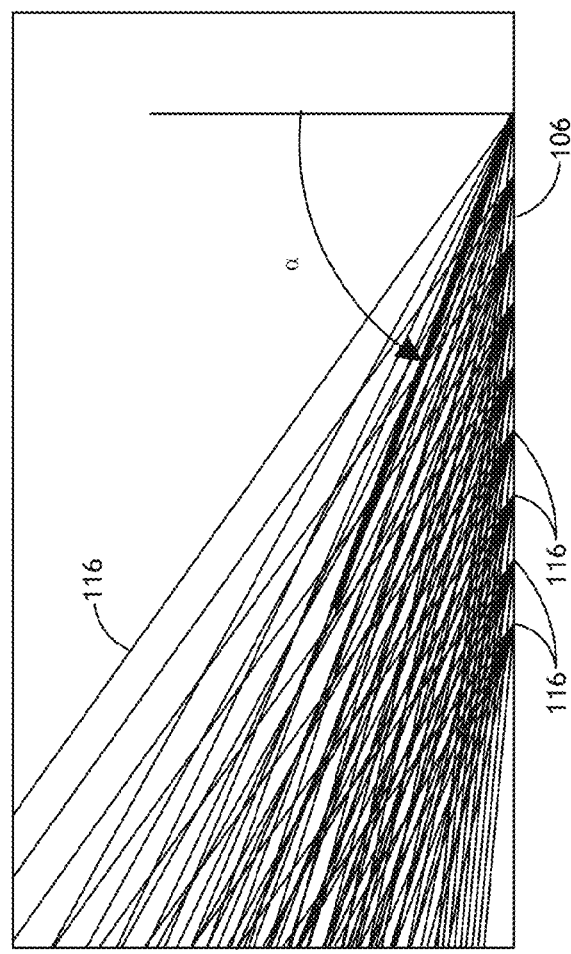
FIG. 4 shows an oblique illumination angle and spot placement in an embodiment of a system for generating a plurality of spots on a surface.

Using the system 100, the plurality of beams 112 may be focused on the surface 106 at an oblique illumination angle. An example of the oblique illumination angle on the surface 106 is provided in FIG. 4. The at least some of the plurality of beams 112 are focused on the surface 106 in a plurality of spots 116. The angle between the surface 106 and the at least some of the plurality of beams 112 is an oblique illumination angle, $\alpha$. The oblique illumination angle may range from 45 degrees to 85 degrees. In one embodiment, the oblique illumination angle may be equal to approximately 70 degrees.

The system 100 may be suitable for generating a plurality of spots 116 having a relatively small spot size in a relatively large field. For example, in the embodiment of the system 100 shown in FIGS. 4 and 5, the system 100 may be used to generate nine spots 116 having a size of 0.8 um each. Each spot 116 is separated by 100 um, and therefore the total field size may be 800 um in the example. The spot 116 size depends on the wavelength, which is 266 nm in this example. The wavelength range can be from 100 nm to 1500 nm. Additional details regarding how the spot size and spot gap may be configured may be found in U.S. Pat. No. 8,194,301, which is hereby incorporated by reference in its entirety.

Figure 5:
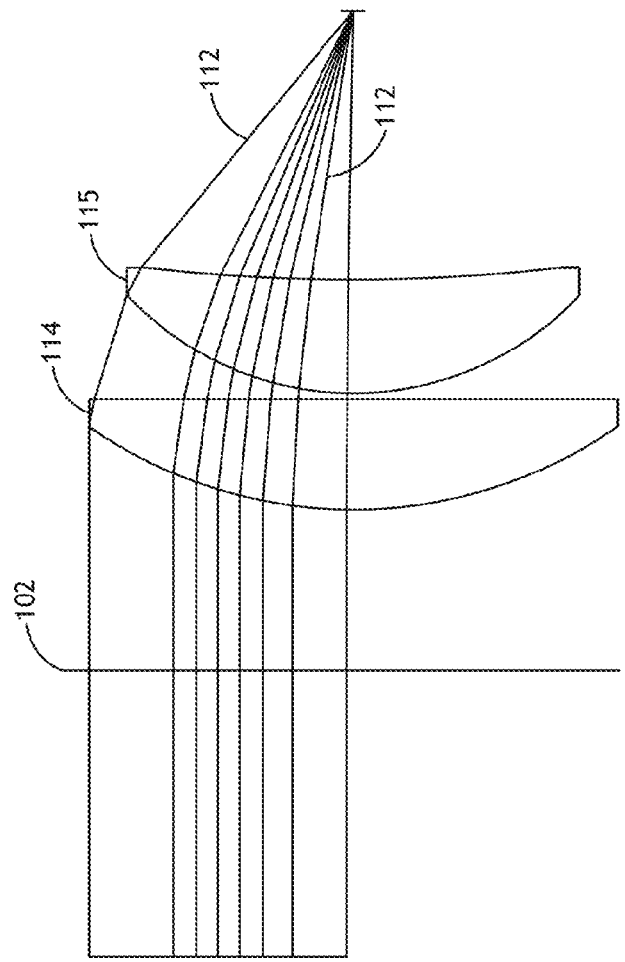
FIG. 5 shows an example system configuration of a system for generating a plurality of spots on a surface.

The system 100 for generating the plurality of spots 116 may include more than one focusing lens 114. For example, FIG. 5 shows an example system configuration for generating the plurality of spots 116 shown in FIG. 4. The system 100 shown in FIG. 5 may include diffractive optical element 102, a first focusing lens 114, and a second focusing lens 115. The diffractive optical element 102 may split a beam, or several beams, into a plurality of beams 112, which are then focused by the first focusing lens 114 and second focusing lens 115 to the plurality of spots 116 shown in FIG. 4.

Figure 6:
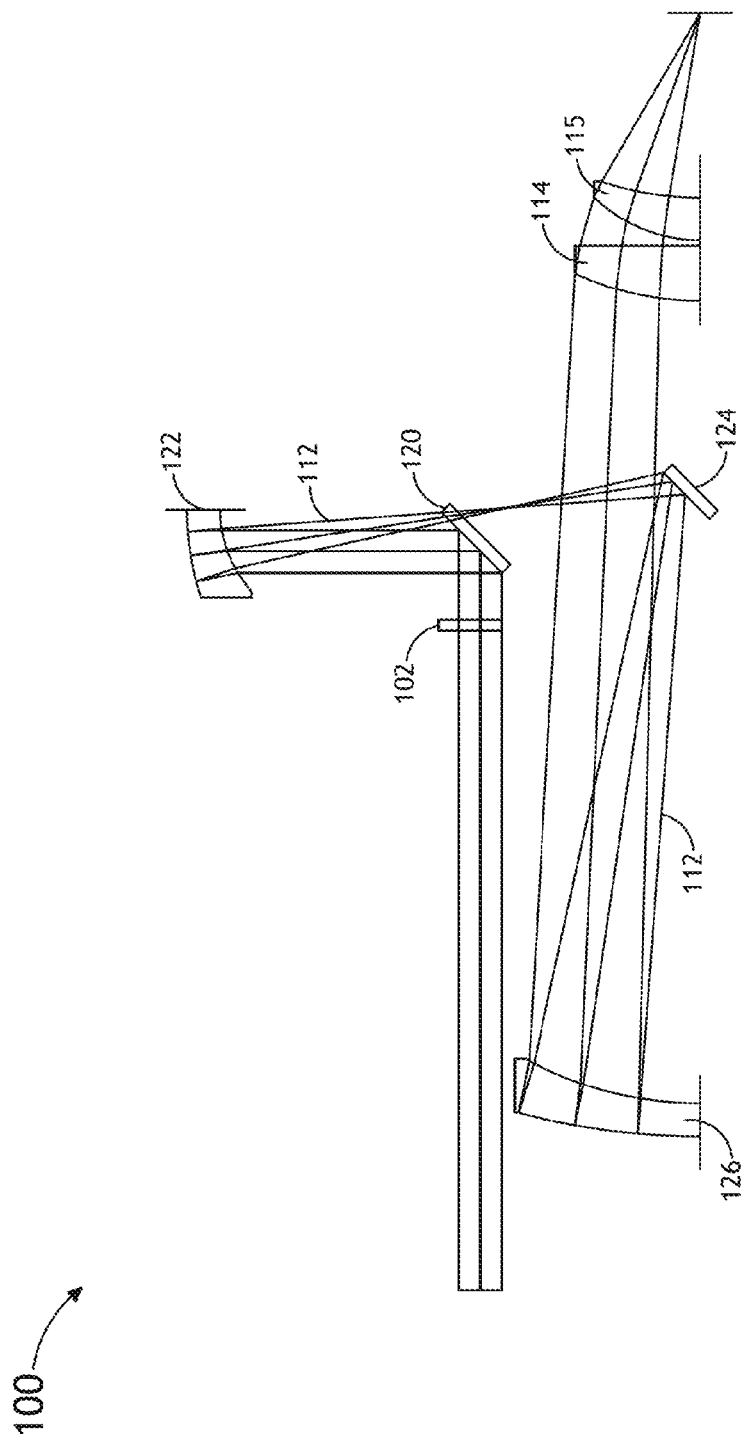
FIG. 6 shows an example system configuration of a system for generating a plurality of spots, the system including reflective elements and refractive elements.

The system 100 may also include additional elements such as mirrors. Similarly, reflective elements and refractive elements may be combined to help correct chromatic aberrations in one embodiment. For example, FIG. 6 shows an embodiment of the system 100 which includes a plurality of mirrors for reflecting the beams 112. The system 100 shown in FIG. 6 may include the diffractive optical element 102, a first mirror 120, a second mirror 122, a third mirror 124, and a fourth mirror 126. The system 100 also includes the first focusing lens 114 and second focusing lens 115. A beam 112 may travel through the diffractive optical element 102 where it may be split into a plurality of beams 112. Only one of the splitted beams is shown in FIG. 6, but all of the beams 112 may pass through a similar path. Then the plurality of beams 112 may be reflected by the folding mirror 120 to the focusing mirror 122. Focusing mirror 122 may be a catadioptric element having both a reflective surface and a refractive surface. Beams 112 are then reflected by another folding mirror 124 to another focusing mirror 126. Focusing mirror 126 may be a catadioptric element having both a reflective surface and a refractive surface. The fourth mirror 126 may reflect at least some of the plurality of beams 112 to the first focusing lens 114 and the second focusing lens 115. At least some of the plurality of beams 112 are then focused by the first focusing lens 114 and second focusing lens 115 to the plurality of spots 116. The example system 100 shown in FIG. 6 may provide a spot 116 configuration as shown in FIG. 2, including eleven spots 116. In the example shown in FIGS. 2 and 6, the spot 116 diameter may be 1.5 um.

Figure 7:
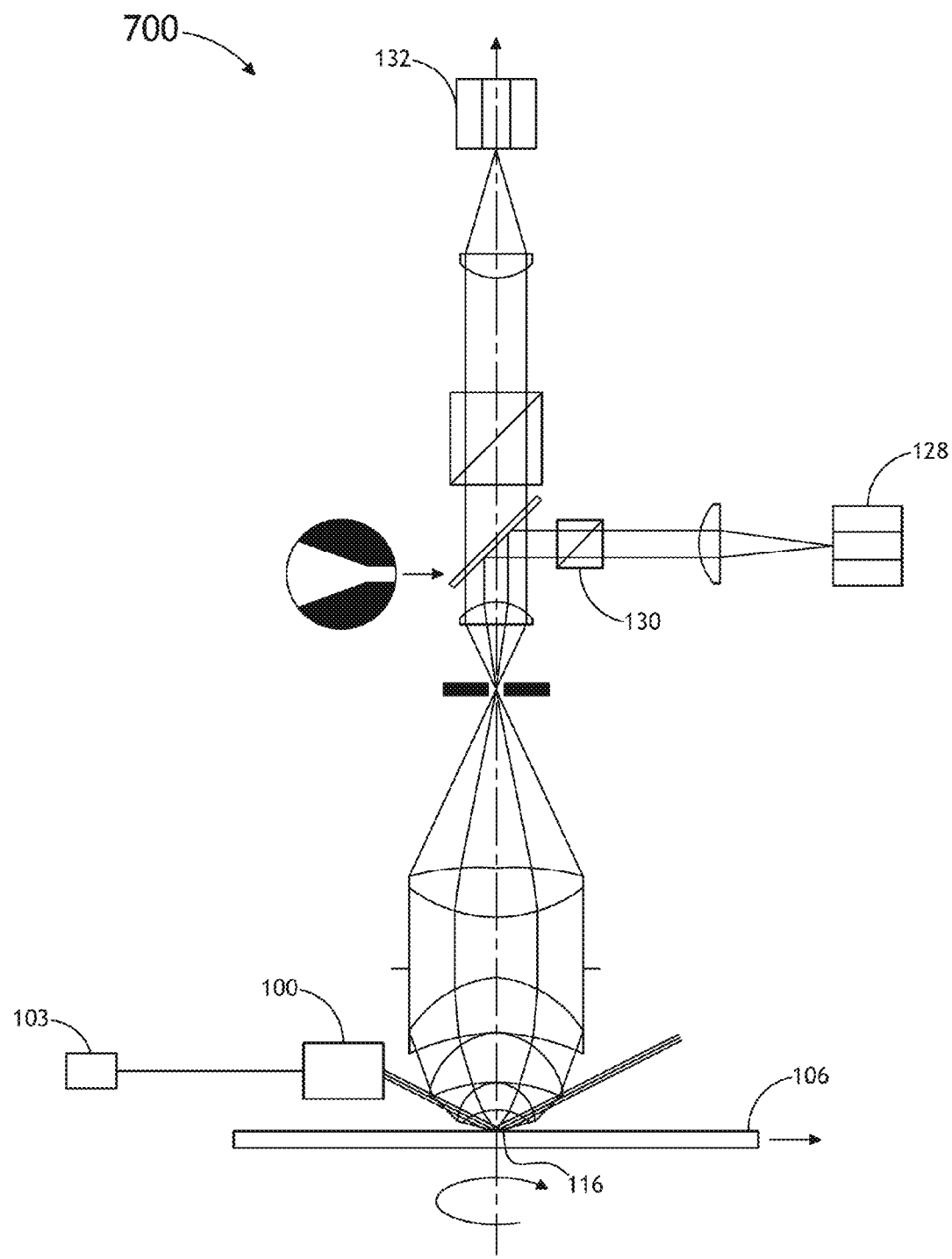
FIG. 7 shows an example of how the system for generating a plurality of spots on a surface may be implemented into an inspection system.

An example of how the system 100 of the present disclosure may be incorporated into an inspection system 700 is provided in FIG. 7. The inspection system 700 shown in FIG. 7 may be a wafer inspection system. The system 100 of the present disclosure may be used with the inspection system 700 to provide multi-spot illumination on the surface 106. For example, illumination source 103 is positioned to provide oblique illumination to the system 100 and the wafer 106. The illumination source 103 provides a beam to the system 100. The system 100, including the diffractive optical element (not shown in FIG. 7) and the lens (not shown in FIG. 7) splits the beam and focuses the beam to generate the plurality of spots 116 on the surface of the wafer 106. The inspection system 700 may include additional elements. For example, the inspection system 700 may include a first detector array 128, polarizers 130, and a second detector array 132, in addition to other elements.

Figure 8:
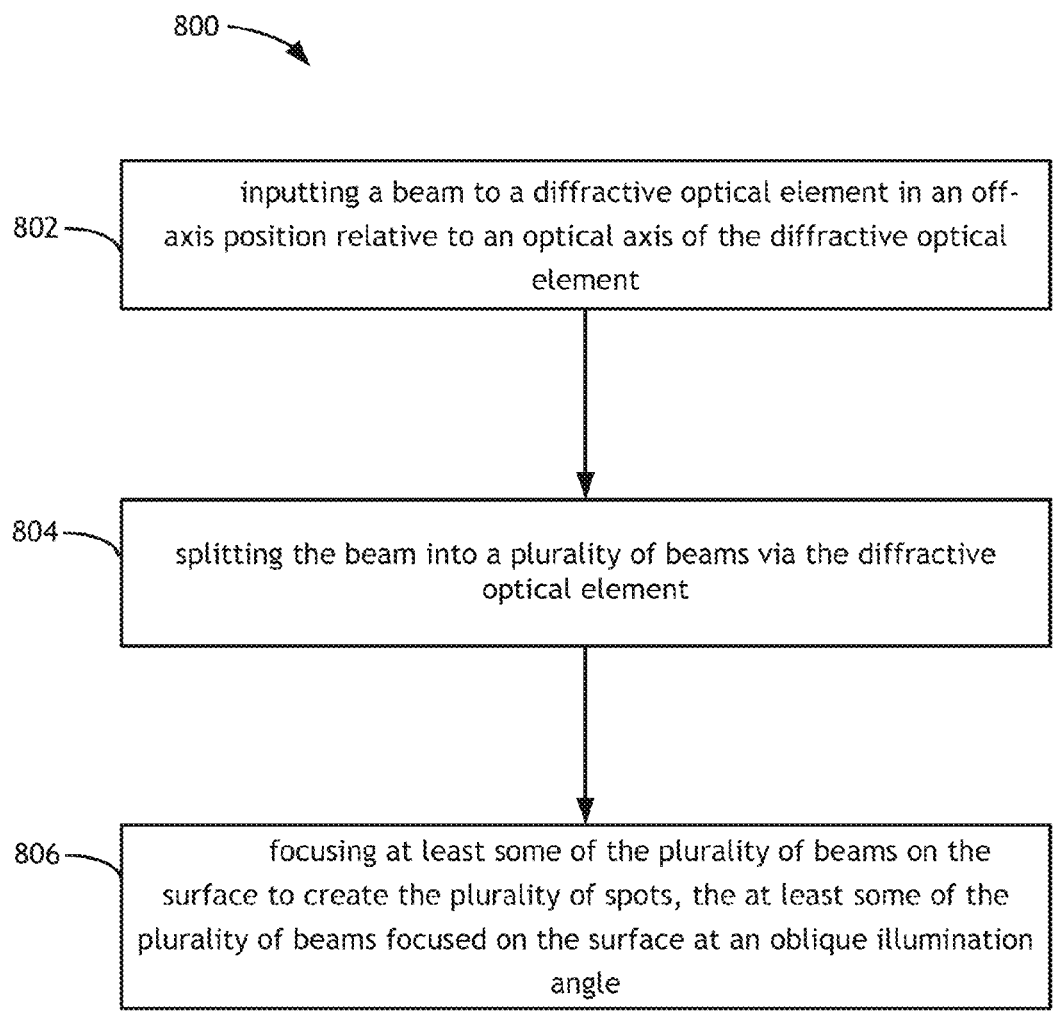
FIG. 8 is a flow chart of a method for generating a plurality of spots on a surface.

The present disclosure is also directed to a method 800 for generating a plurality of spots on a surface, as shown in FIG. 8. The method 800 includes the step of inputting a beam to a diffractive optical element in an off-axis position relative to an optical axis of the diffractive optical element 802. The method 800 also includes the step of splitting the beam into a plurality of beams via the diffractive optical element 804. A further step of the method 800 is focusing at least some of the plurality of beams on the surface to create the plurality of spots, the at least some of the plurality of beams focused on the surface at an oblique illumination angle 806. The method 800 may be useful in systems using an oblique illumination angle. In one embodiment, the method 800 may be used to provide a plurality of spots on an inclined surface.

In the method 800 shown in FIG. 8, at least some of the plurality of beams will be focused on the surface at an oblique illumination angle. The oblique illumination angle of the method 800 may range from 45 degrees to 85 degrees.

The plurality of spots generated by the method 800 shown in FIG. 8 may include a one dimensional spot array. The plurality of spots may be positioned in a radial direction parallel to a linear stage motion direction of the system.

The systems and methods of the present disclosure may be used to generate a plurality of spots on a surface. The surface may include a surface of a wafer in one embodiment. The wafer may include a patterned wafer or an unpatterned wafer. The wafer may be a silicon wafer.

The system and method of the present disclosure may be useful for spiral scanning architecture, including those systems with stationary multi-spot illumination requiring illumination of an inclined surface.

The system and method of the present disclosure may provide a number of advantages. For example, the off-axis configuration may facilitate the provision of a large field size for a large number of spots with a relatively simple design. For example, the system and method of the present disclosure may be useful for large field sizes up to 1 mm in one example (or even greater), as well as small spot sizes of less than 1 um in one example.

In addition, the alignment of the spot array in the radial, rather than tangential, direction helps minimize scan pitch errors and may be advantageous over systems employing other illumination methods. The system and method of the present disclosure may also be useful for systems requiring large laser bandwidth.

The system and method of the present disclosure may also be incorporated into an existing inspection system. For example, the system and method of the present disclosure may be used in an existing inspection system to provide multi-spot illumination with improved sensitivity and throughput. The system and method may also be incorporated into an existing inspection system to minimize pitch error of the existing system. The multi-spot illumination of the system and method of the present disclosure may also overcome issues with the requirement to use limited laser power in order to avoid wafer damage in single spot illumination systems. Similarly, the multi-spot illumination may be helpful in overcoming issues with inspection throughput limited by maximum spindle rotation speed as smaller spot size is required for improved sensitivity, by scanning multiple tracks simultaneously.

It should be recognized that the various steps described throughout the present disclosure may be carried out by a single computing system or, alternatively, a multiple computing system. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

All of the methods described herein may include storing results of one or more steps of the method embodiments in a storage medium. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

It is further contemplated that each of the embodiments of the method described above may include any other step(s) of any other method(s) described herein. In addition, each of the embodiments of the method described above may be performed by any of the systems described herein.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed is:

1. A system for generating an array of focused spots comprising:
   an illumination source, the illumination source configured to generate a beam of illumination;
   a diffractive optical element, the illumination source positioned so as to illuminate the diffractive optical element at normal incidence at an off-axis position with the beam of illumination propagating parallel to an optical axis of the diffractive optical element, the diffractive optical element configured to split the beam of illumination into a plurality of diffracted beams; and
   a focusing lens, the focusing lens positioned adjacent to the diffractive optical element along the optical axis, the focusing lens configured to focus at least some of the plurality of diffracted beams onto a surface of a wafer into a plurality of elongated spots positioned along a radial direction of the wafer, wherein a direction of elongation of at least some of the plurality of elongated spots is aligned along the radial direction, wherein the focusing lens and the diffractive optical element are arranged to cause at least some of the plurality of diffracted beams from the diffractive optical element to impinge onto the surface of the wafer at an oblique illumination angle relative to the surface of the wafer.

2. The system of claim 1, wherein the oblique illumination angle ranges from 45 degrees to 85 degrees.

3. The system of claim 1, wherein the plurality of spots along the optical axis includes a one dimensional spot array.

4. The system of claim 1, wherein the plurality of spots are positioned in a radial direction, the radial direction parallel to a stage motion direction of the system.

5. The system of claim 4, wherein an incident plane of the at least some of the plurality of beams is parallel to the radial direction.

6. The system of claim 1, wherein the diffractive optical element includes a diffractive optical element having concentric circles of grating grooves, a grating pitch of the grating grooves a function of a radius of the diffractive optical element.

7. The system of claim 1, wherein the surface includes a surface of a silicon wafer.

8. The system of claim 1, wherein illumination source comprises:
   a laser.

9. A method for generating an array of focused spots comprising:
   inputting a beam from an illumination source at normal incidence to a diffractive optical element in an off-axis position, the beam propagating parallel to an optical axis of the diffractive optical element;
   splitting the beam into a plurality of beams via the diffractive optical element; and
   focusing, with a focusing lens positioned adjacent to the diffractive optical element along the optical axis, at least some of the plurality of beams onto a surface of a wafer to create a plurality of elongated spots positioned along a radial direction of the wafer, wherein a direction of elongation of at least some of the plurality of elongated spots is aligned along the radial direction, the at least some of the plurality of beams focused on the surface at an oblique illumination angle relative to the surface of the wafer.

10. The method of claim 9, wherein the oblique illumination angle ranges from 45 degrees to 85 degrees.

11. The method of claim 9, wherein the plurality of spots along the optical axis includes a one dimensional spot array.

12. The method of claim 9, wherein the plurality of spots are positioned in a radial direction, the radial direction parallel to a stage motion direction of the system.

13. The method of claim 12, wherein an incident plane of the at least some of the plurality of beams is parallel to the radial direction.

14. The method of claim 9, wherein the diffractive optical element includes a diffractive optical element having concentric circles of grating grooves, a grating pitch of the grating grooves a function of a radius of the diffractive optical element.

15. The method of claim 9, wherein the surface includes a surface of a silicon wafer.

16. A system for generating an array of focused spots comprising:
   an illumination source configured to generate a beam of illumination;
   the diffractive optical element, the illumination source positioned so as to illuminate the diffractive optical element at normal incidence at an off-axis position with the beam of illumination propagating parallel to an optical axis of the diffractive optical element, the diffractive optical element configured to split the beam into a plurality of diffracted beams; and
   a focusing lens, the focusing lens positioned adjacent to the diffractive optical element along the optical axis, the focusing lens configured to focus at least some of the plurality of diffracted beams onto a surface of a wafer into a plurality of elongated spots positioned along a radial direction of the wafer, wherein a direction of elongation of at least some of the plurality of elongated spots is aligned along the radial direction, the at least some of the plurality of diffracted beams focused on the surface of the wafer at an oblique illumination angle relative to the surface of the wafer, wherein the plurality of spots are positioned along the radial direction, the radial direction parallel to a stage motion direction of the system, wherein an incident plane of the at least some of the plurality of diffracted beams is along the radial direction.

17. The system of claim 16, wherein the oblique illumination angle ranges from 45 degrees to 85 degrees.

18. The system of claim 16, wherein the plurality of spots along the optical axis includes a one dimensional spot array.

19. The system of claim 16, wherein the diffractive optical element includes a diffractive optical element having concentric circles of grating grooves, a grating pitch of the grating grooves a function of a radius of the diffractive optical element.

20. The system of claim 16, wherein the surface includes a surface of a silicon wafer.

* * * * *